United States Patent [19]

Boyer

[11] Patent Number: 4,618,686
[45] Date of Patent: Oct. 21, 1986

[54] PROCESS FOR DEHALOGENATION OF ARYL AND ALPHA-ARALIPHATIC HALIDES

[75] Inventor: Stephen K. Boyer, Far Hills, N.Y.

[73] Assignee: Ciba-Geigy Corporation, Ardsley, N.Y.

[21] Appl. No.: 655,279

[22] Filed: Sep. 27, 1984

[51] Int. Cl.$^4$ .................... C07B 61/00; C07D 319/24
[52] U.S. Cl. ...................... 549/360; 210/57; 210/749; 210/755; 210/909; 544/242; 544/264; 546/257; 546/139; 546/152; 548/215; 548/335; 548/373; 548/469; 570/204; 564/305; 564/412; 585/254; 585/469
[58] Field of Search ............... 585/469, 254, 400, 935; 564/305, 412; 568/103, 796, 797; 210/57, 749, 755, 909; 544/242, 334, 264; 570/204; 546/257; 548/215, 335, 373; 549/360

[56] References Cited

U.S. PATENT DOCUMENTS

| | | | |
|---|---|---|---|
| 2,725,405 | 11/1955 | Britton et al. | 570/204 |
| 3,054,830 | 9/1962 | Luvisi et al. | 585/469 |
| 3,064,059 | 11/1962 | Luvisi et al. | 564/469 |
| 3,652,608 | 3/1972 | Fenton | 560/213 |
| 4,022,795 | 5/1977 | Bamfield et al. | 564/305 |
| 4,351,978 | 9/1982 | Hatano et al. | 585/469 |

OTHER PUBLICATIONS

J. R. Kosak, "Hydrogenation of Haloaromatic Nitro Compounds", Catalysis in Organic Synthesis, 107–117, William H. Jones, editor, 1980.
V. M. Plets: CA, 31, 4965$^9$ (1937).
Nichols A. Cortese & Richard F. Heck: J. Org. Chem., 42, No. 22, 3491–3494 (1977).
Tetrahedron Letters, vol. 26, No. 31, pp. 3677–3680 (1985).
Journal of Organic Chemistry, 50:3408 (1985).
Morrison, et al., Organic Chemistry, Fourth ed., New York University, pp. 1269–1271.
Tetrahedron Letters, vol. 25, No. 40, pp. 4565–4568, 1984.

*Primary Examiner*—Veronica P. Hoke
*Attorney, Agent, or Firm*—Michael W. Glynn; Irving M. Fishman

[57] ABSTRACT

Process for the dehalogenation of aryl and alpha-araliphatic halides comprising contacting the aryl halide or alpha-araliphatic halide with hypophosphite salt, in the presence of a catalytic amount of a noble metal catalyst. This process is useful in the field of organic synthesis and for the removal of environmentally hazardous aryl and alpha-araliphatic halides, including polychlorinated biphenyls and dibenzo-p-dioxins.

15 Claims, No Drawings

PROCESS FOR DEHALOGENATION OF ARYL AND ALPHA-ARALIPHATIC HALIDES

BACKGROUND OF THE INVENTION

The present invention relates to a convenient process for the dehalogenation of aromatic and alpha-araliphatic halides which is simple, economic and eliminates the hazards of explosion and the like associated with the use of hydrogen gas or alkali metal alkoxides.

It is known, for example, in U.S. Pat. No. 4,337,368 to dehalogenate organic compounds, including polychlorinated biphenyl and chlorinated benzenes, with a reagent comprising polyethylene glycol, sodium and oxygen, presumably in the form of a sodium glycolate-superoxide complex, to form the corresponding hydroxylated biphenyls and phenols. An alternate technique is disclosed by Colebourne et al., Ger. Offen. No. 2,127,182, wherein chlorinated organics, including hexachlorobenzene, are reduced with gaseous hydrogen in the presence of platinum/aluminum oxide catalyst at elevated temperatures, specifically reciting 375°. In Japanese Kokai No. 81.133,221, Chemical Abstract Vol. 96 No. 51959j, the dechlorination of 2-chlorotoluene is described with gaseous hydrogen under a pressure of 0.6 Kg/cm$^2$ and an aqueous alkali metal hydroxide in the presence of palladium on carbon for over three hours at 70°.

The instant invention is based upon the discovery of a practical, economic process for the dehalogenation of aromatic and alpha-araliphatic halides in the presence of a hypophosphite salt and a hydrogenation catalyst in an aqueous or aqueous/organic or liquid alkanoic acid medium, preferably in the presence of a base.

DETAILED DESCRIPTION OF THE INVENTION

One embodiment of the invention relates to the dehalogenation of aromatic and alpha-araliphatic halides with a hypophosphite salt in the presence of a catalytic amount of a hydrogenation catalyst in an aqueous, aqueous/organic or liquid alkanoic acid medium at a temperature between 0° C. and the boiling point of the reaction medium, in the presence or absence of a base.

Where the product of the dehalogenation reaction is a commercially valuable product, such as a chemical synthesis intermediate or final product, it may be recovered from the reaction medium by distillation, crystallization, evaporation, or other conventional separation techniques.

Where the dehydrohalogenation is effected for purposes of removing environmentally hazardous aromatic halides and alpha-araliphatic halides from the environment, the resulting dehalogenated product may be disposed of by incineration or other conventional disposal techniques.

The nature of the aromatic and alpha-araliphatic halides useable in the instant process can vary widely in aromatic structure and include aromatic nucleus halogenated and/or alpha-halo aliphatic substituted, such as halo-methyl substituted: phenyl, naphthyl, biphenyl, anthracenyl, phenanthrenyl, quinolinyl, isoquinolinyl, carbazole, purinyl, pyridinyl, pyrimidinyl, pyrazodyl, imidazolyl, furanyl, oxazolyl, indolyl, benzofuranyl, quinolinyl, benzoquinolinyl isoquinolinyl, or dibenzodioxinyl, which are further unsubstituted or substituted, for example, by cyano, nitro, —NHR, —N(R)$_2$, —COOR, —CONHR, —CON(R)$_2$, —OR, —C(O)R, —OOC—R, —NHC(O)—R, —SO$_2$R, —NHC(O)—OR, —SO$_2$—R, —SO$_3$R, —SR or —R, where R is hydrogen, or an aryl, aliphatic or araliphatic group; and where the aromatic or alpha-araliphatic halide is polynuclear, one or more rings thereof may be at least partially saturated. During the dehalogenation process, certain substituents, such as epoxy, aldehyde and keto groups may be reduced to the corresponding hydroxy group. Where the aromatic moiety contains an olefinic double bond, the alkenylene moiety may be characteristically reduced to the corresponding alkylene moiety. Nitro groups are characteristically reduced to the corresponding amine during dehalogenation. Amine oxide groups are similarly reduced to the corresponding amine, as are azides. Also, benzoxy groups may be characteristically removed by dehydrogenolysis to result in the corresponding hydroxy group, and benzoxycarbamate substituents are reduced to the corresponding amine. Non-alpha (to an aromatic moiety) polyhalo aliphatic carbon atoms tend to be dehalogenated to the corresponding mono-halo derivative. Further, aliphatic mono- and poly-halogenated carbon atoms alpha to an aromatic nucleus are dehalogenated during the reaction. Mixtures of aromatic and/or alpha-araliphatic halides may be used.

By halogenated, and halo, are meant chloro, fluoro, bromo or iodo, especially chloro or bromo, substituents.

By aryl is preferably meant phenyl which is unsubstituted or substituted by lower alkyl, lower alkoxy, carboxy, sulfoxy, amino, mono- or di-(lower alkyl)amino, cyano, lower alkanoyloxy, amido, mono- or di-(lower alkyl) amido, hydroxy or halo.

By aliphatic is preferably meant lower alkyl or lower alkenyl which are unsubstituted or substituted by lower alkoxy, carboxy, sulfoxy, amino, mono- or di-(lower alkyl)amino, cyano, lower alkanoyloxy, amido, mono- or di-(lower alkyl)amido, hydroxy or halo.

By araliphatic is preferably meant phenyl-substituted lower alkyl, such as benzyl or phenethyl, which are unsubstituted or substituted by lower alkoxy, carboxy, sulfoxy, amino, mono- or di-(lower alkyl)amino, cyano, lower alkanoyloxy, amido, mono- or di-(lower alkyl)amido, hydroxy or halo.

A particularly preferred embodiment of the invention relates to the dehalogenation of mono- and polyhalogenated aromatic hydrocarbons and dibenzodioxins, including "PCB"s and "dioxins". PCBs are chlorinated biphenyls long used as dielectric fluids in electrical equipment and the like. As of July 1, 1979, the Environmental Protection Act regulations, issued by the U.S. Environmental Protection Agency, defined as "PCB contaminated" any material containing more than 50 pmm of a mono-, di- or polychlorinated biphenyl. Such PCB contaminated materials can be used in the instant process to remove the halogenated component thereof by dehalogenation. Dioxins as used herein means polychlorinated dibenzodioxins, also determined to be environmentally hazardous, especially the 2,3,6,7-tetrachloro-dibenzo-p-dioxin. These materials can also be used in the instant process to remove the halogenated component thereof by dehalogenation.

Preferred catalysts include metal hydrogenation catalysts such as Raney nickel, and noble metal hydrogenation catalysts, such as palladium and platinum catalysts. A most preferred catalyst is palladium. Advantageously, the catalyst is present on a suitable support, e.g. carbon.

Reaction temperatures can vary widely, e.g. from 0° C. to the boiling point of the reaction medium, characteristically about 100° C. Preferably, the reaction is conducted between about 20° C. to about 100° C., most preferably at 50° C. to 80° C.

The reaction medium is aqueous, aqueous/organic or liquid alkanoic acid medium. The nature of the organic medium is not critical, and if the starting material is a liquid at the reaction temperature, no further organic medium need ordinarily be present. Suitable organic diluents include tetrahydrofuran, dioxane, benzene, toluene, and the like. A liquid alkanoic acid medium, such as glacial acetic acid, or propionic acid, may be used where substantially anhydrous conditions are desired.

The nature of the cation in the hypophosphite salt is not critical. Suitable salts include the alkali metal, alkaline earth metal, ammonium and amine salts, e.g. the mono-, di-, tri- and tetra- (lower alkyl)amine salts, thereof. Preferred salts include the alkali metal salts, most preferably the sodium salt.

The halogenated starting material is desirably placed into intimate contact with an aqueous or aqueous/organic solution of the hypophosphite salt, in the presence of the hydrogenation catalyst, for example by agitation, such as stirring or sonication.

Further, the reaction is desirably carried with the removal of hydrogen halide by-product. The hydrogen halide can be removed, for example, by the passage of an inert gaseous material, such as nitrogen, through the reaction medium or by the use of a base. Suitable basic materials include alkali or alkaline earth metal hydroxides, bicarbonates or carbonates; ammonia, e.g. in the form of ammonium hydroxide; or amines, including mono-, di- or tri-(lower alkyl)amines or quaternary ammonium hydroxides, such as tetra-methyl ammonium hydroxide. Similarly, salts of carboxylic acids, especially lower alkanoic acids, such as alkali metal salts, for example, sodium acetate can be used to remove hydrohalic acids released during the reaction.

The reaction can be conducted in acidic, neutral or basic media. A neutral or basic medium is preferred. Where an acidic medium is used, such as a liquid alkanoic acid medium, the released hydrohalic acid is preferably removed with a carboxylate salt.

The following examples are presented only for purposes of illustration and are not intended to limit the scope of the invention. Unless otherwise noted, all parts are parts by weight.

EXAMPLE 1

4 Grams of polychorinated biphenyl transformer oil (ASKAREL) containing approximately up to 70% PCBs was dissolved in 25 ml of tetrahydrofuran and mixed with 25 g potassium carbonate dissolved in 50 ml water, and 0.5 g of 5% palladium on carbon. The mixture was stirred and warmed to 50° C. To this mixture, while stirring, was added a solution of 10 g sodium hypophosphite monohydrate in 20 ml water dropwise over a period of one hour. Subsequently, an additional 5 g of sodium hypophosphite monohydrate in 10 ml water was added dropwise over a period of 30 minutes. The catalyst was filtered off, the reaction mixture was mixed with 100 ml diethyl ether, the phases separated, the aqueous phase was extracted with 100 ml diethyl ether in 50 ml portions and the organic phases combined. After drying the organic phase with magnesium sulfate, the organic phase was concentrated to yield 0.85 g of biphenyl. A GC analysis made on both the starting material and the reaction product established that all detectable PCB's had been removed.

EXAMPLE 2

4 Grams of polychlorinated biphenyl transformer oil (ASKAREL) containing approximately up to 70% PCBs was dissolved in 40 ml of tetrahydrofuran and mixed with 16 g anhydrous sodium carbonate dissolved in 50 ml of water, and 1 g of 5% palladium on carbon. The mixture was stirred and warmed to 50° C. and 16 g of sodium hypophosphite in 30 ml water was added to the reaction material dropwise over a period of one hour. After one hour a GC analysis on the reaction mixture showed a loss of many peaks in comparison with a GC analysis run on the untreated PCB containing transformer oil. After 5 hours at 50° C., the reaction mixture was allowed to cool to 23° C., the mixture filtered to recover the catalyst, and the filter cake washed with a mixture of 50 ml tetrahydrofuran and 50 ml water. The filtrate and washings were combined and diluted with 200 ml water, the organic layer separated and the aqueous layer back-extracted with 15 ml diethyl ether. The combined organic extracts were washed with 100 ml saturated sodium chloride, the organic layer was separated, dried over 15 g magnesium sulfate, filtered and evaporated to give 1.2 g of a white solid biphenyl of 80% purity. By CG analysis, no PCBs remained.

EXAMPLE 3

To 1.1 grams of chlorobenzene in 10 ml acetone was added 2 g potassium carbonate and 200 mg of 5% palladium on carbon. The reaction mixture was heated to about 50° C. and stirred and 1.2 g sodium hypophosphite monohydrate in about 3 ml water was added. After about 1 hour, CG analysis established that virtually all of the chlorobenzene was converted to benzene in a yield in excess of 90%, and only a trace of chlorobenzene remained.

EXAMPLE 4

To a solution of 3.1 g of 4,4'-dibromo biphenyl in 30 ml tetrahydrofuran was added 3.5 g sodium carbonate and 400 mg of 5% palladium on carbon. To this reaction mixture there was added 2.5 g sodium hypophosphite monohydrate in about 20 ml water. After about one hour, a GC analysis established that all of the starting material had reacted to yield primarily biphenyl with a trace amount of p-mono-bromobiphenyl.

EXAMPLE 5

Following the procedure of Example 3, benzyl chloride was reduced to toluene in a yield in excess of 90%.

Similarly, p-benzoxybenzylchloride was reduced in accordance with the procedure of Example 3, to give a mixture of p-cresol and p-benzoxytoluene in a ratio of approximately 49% p-cresol and 51% p-benzoxytoluene.

EXAMPLE 6

Using 10 mmole of halogenated starting material dissolved in approximately 25 ml tetrahydrofuran, and added thereto 1.17 g (11 mmol) sodium carbonate and approximately 200 mg 5% palladium on carbon, a solution of sodium hypophosphite monohydrate (approximately 11 mmol) in about 5 ml water per equivalent of halogen in the starting material is added dropwise over 10–15 minutes to the rapidly stirred reaction mixture maintained at a temperature of about 50°–65° C. The reaction product is then diluted with about 50 ml diethyl ether, filtered to remove catalyst and the filtrate diluted with about 100 ml water. The organic layer is separated from the aqueous layer and the aqueous layer is back extracted with 50 ml diethyl ether. The organic extracts are combined, dried with magnesium sulfate and concentrated in vacuo to isolate the reaction product. In this manner the following products are dehalogenated:

```
p-bromobenzylchloride to toluene
p-bromoaniline to aniline
p-bromoacetanilide to acetanilide
p-bromophenol to phenol
2-chloronaphthalene to naphthalene
3-chloropyridine to pyridine
6-chloroquinoline to quinoline
p-bromophenetole to phenetole
9-bromophenanthrene to phenanthrene
2-bromopyrimidine to pyrimidine
5-bromoindole to indole
3-bromofuran to furan
p-chlorobenzonitrile to benzonitrile
ethyl p-chlorobenzoate to ethyl benzoate.
```

What is claimed is:

1. A process for the dehalogenation of a compound selected from a (carbocyclic or heterocyclic) aromatic halide and an alpha-(carbocyclic or heterocyclic) aromatic-aliphatic halide wherein said carbocyclic or heterocyclic aromatic group is selected from
phenyl, naphthyl, biphenyl, anthracenyl, phenanthrenyl, quinolinyl, isoquinolinyl, carbazole, purinyl, pyridinyl, pyrimidinyl, pyrazolyl, imidazolyl, furanyl, oxazolyl, indolyl, benzofuranyl, benzoquinolinyl, and dibenzodioxinyl,
each of said carbocyclic or heterocyclic aromatic groups being further unsubstituted or further substituted by a substituent selected from
cyano, nitro, —NHR, —N(R)₂, —COOR, —CONHR, —CON(R)₂, —OR, —C(O)R, —OOCR, —NHC(O)R, —SO₂R, —NHCOOR, —SO₃R, —SR, and R,
wherein R is hydrogen, or a phenyl which is unsubstituted or further substituted with a substituent selected from lower alkyl, lower alkoxy, carboxy, sulfoxy, amino, mono-lower alkylamino, di-lower alkylamino, cyano, lower alkanoyloxy, amido, mono-alkylamido, dialkylamido, hydroxy, and halo, or R is an aliphatic selected from lower alkyl or lower alkenyl, each of which is unsubstituted or substituted by lower alkoxy, carboxy, sulfoxy, amino, mono-lower alkylamino, di-lower alkylamino, cyano, lower alkanoyloxy, amido, mono-lower alkylamido, di-lower alkylamido, hydroxy or halo, or R is a phenyl-lower alkyl which is unsubstituted or substituted by lower alkoxy, carboxy, sulfoxy, amino, mono-lower alkylamino, di-lower alkylamino, cyano, lower alkanoyloxy, amido, mono-lower alkylamido, di-lower alkylamido, hydroxy or halo,
said aliphatic portion of said alpha-(carbocyclic or heterocyclic) aromatic-aliphatic halide being lower alkyl which is unsubstituted or further substituted by lower alkoxy, carboxy, sulfoxy, amino, mono-lower alkylamino, di-lower alkylamino, cyano, lower alkanoyloxy, amido, mono-lower alkylamido, di-lower alkylamido, hydroxy or halo, and when said compound is polynuclear, the analogs thereof having at least one but not all of the nuclear rings partially or totally saturated, comprising:
reacting said compound with a stoichiometric excess of a hypophosphite salt in the presence of a catalytic amount of a hydrogenation catalyst in an aqueous, aqueous/organic, or liquid alkanoic acid medium at a temperature between 0° C. and the boiling point of the medium in the presence of a stoichiometric excess of a base.

2. A process according to claim 1, wherein the hydrogenation catalyst is Raney nickel or a noble metal hydrogenation catalyst.

3. A process according to claim 1, wherein the hydrogenation catalyst is palladium.

4. A process according to claim 3, wherein the palladium is supported on carbon.

5. A process according to claim 1, wherein said compound is a carbocyclic aromatic halide.

6. A process according to claim 1, wherein said carbocyclic or heterocyclic aromatic halide is selected from mono- and polyhalogenated carbocyclic aromatic compounds as defined in claim 1 and mono- and polyhalogenated p-dibenzodioxins.

7. A process according to claim 6, wherein the carbocyclic or heterocyclic aromatic halide is a chlorinated biphenyl.

8. A process according to claim 1, wherein the compound is an aromatic nucleus halogenated halide.

9. A process according to claim 1, wherein the compound is an alpha-(carbocyclic or heterocyclic)aromatic-aliphatic halide.

10. A process according to claim 1, wherein the hypophosphite is an alkali metal hypophosphite.

11. A process according to claim 6, wherein the catalyst is a palladium catalyst.

12. A process according to claim 11, wherein the reaction is conducted in an aqueous or aqueous/organic medium.

13. A process according to claim 3, wherein the reaction is conducted in an aqueous or aqueous organic medium.

14. A process for the dehalogenation of a compound selected from mono- and polyhalogenated biphenyl and p-dibenzodioxin which are further unsubstituted or substituted by a substituent selected from
cyano, nitro, —NH(R), —N(R)₂, —COOR, —CONHR, —CON(R)₂, —OR, —C(O)R, —OOCR, —NHC(O)R, —SO₂R, —NHCOOR, —SO₃R, —SR, and —R,
wherein R is hydrogen; or phenyl, lower alkyl, lower alkenyl, or phenyl-lower alkyl, each of which is unsubstituted or substituted by lower alkoxy, carboxy, sulfoxy, amino, mono-lower alkylamino, di-lower alkylamino, cyano, lower alkanoyloxy, amido, mono-lower alkylamido, di-lower alkylamido, hydroxy, or halo; or a phenyl substituted with lower alkyl;
comprising:
reacting said compound with a stoichiometric excess of a hypophosphite salt in the presence of a catalytic amount of a palladium on carbon catalyst in an aqueous, aqueous/organic, or liquid alkanoic medium, at a temperature between 0° C. and the medium boiling point, in the presence of a stoichiometric excess of a base capable of neutralizing any H-halide which may be produced.

15. A process according to claim 14 wherein the compound is a mono- or polychlorinated biphenyl or a mono- or polychlorinated p-dibenzodioxin.

* * * * *